United States Patent [19]

Higuchi et al.

[11] Patent Number: 5,424,477
[45] Date of Patent: Jun. 13, 1995

[54] PREPARATION PROCESS OF α-ASPARTYL-L-PHENYLALANINE METHYL ESTER

[75] Inventors: Chojiro Higuchi; Ikumi Kitada; Akinori Nagatomo; Katashi Enomoto; Masanobu Ajioka; Akihiro Yamaguchi, all of Kanagawa, Japan

[73] Assignee: Mitsui Toatsu Chemicals Incorporated, Tokyo, Japan

[21] Appl. No.: 128,739

[22] Filed: Sep. 30, 1993

Related U.S. Application Data

[63] Continuation of Ser. No. 871,501, Apr. 21, 1992, abandoned.

[30] Foreign Application Priority Data

Apr. 24, 1991 [JP] Japan ................... 3-094091
May 21, 1991 [JP] Japan ................... 3-116106

[51] Int. Cl.$^6$ ............................ C07C 209/06
[52] U.S. Cl. .................................. 560/40
[58] Field of Search ........................... 560/40

[56] References Cited

U.S. PATENT DOCUMENTS

| | | |
|---|---|---|
| 3,808,190 | 4/1974 | Dahlmans et al. |
| 3,879,372 | 4/1975 | Boesten ................... 560/40 |
| 4,638,081 | 1/1987 | Elefante ................... 560/40 |
| 4,900,863 | 2/1990 | Schmidt et al. |
| 4,994,605 | 2/1991 | Kishimoto et al. ......... 560/40 |

FOREIGN PATENT DOCUMENTS

| | | |
|---|---|---|
| 27319 | 4/1981 | European Pat. Off. |
| 2608174 | 7/1977 | Germany |
| 49-6305 | 2/1974 | Japan |
| 49-41425 | 11/1974 | Japan |
| 57-40071 | 11/1976 | Japan |
| 57-25537 | 5/1982 | Japan |
| 57-25538 | 5/1982 | Japan |

OTHER PUBLICATIONS

Pine et al., "Organic Chemistry", 4th Ed. (1980) McGraw-Hill Book Company, N.Y., pp.804–805.
House, "Modern Synthetic Reactions", 2 Ed., (1972) Benjamin/Cummings Pub., Mass. pp. 1–3.

Primary Examiner—Johann Richter
Assistant Examiner—John Peabody
Attorney, Agent, or Firm—Burns, Doane, Swecker & Mathis

[57] ABSTRACT

α-L-Aspartyl-L-phenylalanine methyl ester (α-APM) is prepared by catalytic hydrogenation of N-benzyloxycarbonyl-α-L-aspartyl-L-phenylalanine methyl ester (Z-α-APM). The catalytic hydrogenation is conducted in an aqueous suspension containing the Z-α-APM in the form of particles whose average particle size is not greater than 800 μm. The starting Z-α-APM may contain up to 30 wt. % of its β-isomer provided that the process additionally includes recrystallization of the α-APM, collection of the α-APM by filtration and recycling of the filtrate for use in the aqueous suspension of Z-α-APM.

6 Claims, No Drawings

PREPARATION PROCESS OF α-ASPARTYL-L-PHENYLALANINE METHYL ESTER

This application is a continuation of application Ser. No. 07/871,501, filed Apr. 21, 1992, now abandoned.

BACKGROUND OF THE INVENTION

1) Field of the Invention

This invention relates to a process for the preparation of α-L-aspartyl-L-phenylalanine methyl ester (hereinafter abbreviated as "α-APM").

α-APM is widely known as a dipeptide sweetener. It has good sweetness characteristics and a high degree of sweetness close to 200 times the sweetness of sucrose, whereby its demand as a dietetic sweetener is increasing considerably.

2) Description of the Related Art

α-APM is a dipeptide compound formed of L-aspartic acid and L-phenylalanine methyl ester. Although a number of processes have already been known, centering around chemical preparation processes, as to its preparation, the common process is to use an N-protected-L-aspartic anhydride and L-phenylalanine methyl ester as starting materials.

For example, a process is known in which α-APM is obtained by reacting N-benzyloxycarbonyl-L-aspartic anhydride and a salt of L-phenylalanine methyl ester in an inert solvent containing a base in an amount at least equivalent to the salt of L-phenylalanine methyl ester, dissolving the thus-formed N-benzyloxycarbonyl-α-L-aspartyl-L-phenylalanine methyl ester (hereinafter as abbreviated as "Z-α-APM") as an alkali salt in water, acidifying the solution, extracting the solution with a water-immiscible organic solvent and then subjecting the extract to catalytic hydrogenation in methanol (U.S. Pat. 3,808,190). In this process, however, hydrolysis of Z-α-APM takes place due to the use of the acid and alkali upon the extraction so that α-L-aspartyl-L-phenylalanine (hereinafter abbreviated as "α-AP" is byproduced subsequent to the catalytic hydrogenation.

Further, Japanese Patent Publication No. 40071/1976 discloses a process for obtaining α-APM, in which Z-α-APM obtained by condensation of N-benzyloxycarbonylaspartic anhydride and L-phenylalanine methyl ester in an organic solvent is subjected to catalytic hydrogenation in acetic acid or a mixed solution of acetic acid and water as a solvent. This process, however, requires removal of acetic acid by distillation in order to isolate e-APM after the reduction. 3-Benzyl-6-carboxymethyl-2,5-diketopiperazine (hereinafter abbreviated as "DKP") which does not have sweetness is however formed during the distillation, leading to a reduction in yield and deterioration in quality.

Japanese Patent Publication No. 25537/1982 discloses a process for the preparation of α-APM, in which Z-α-APM is reduced using a platinum-group catalyst in the presence of an aqueous solution of a mineral acid and then neutralizing the aqueous solution of the resultant reaction product. This process, however, is accompanied by the byproduction of α-AP due to hydrolysis of the resulting α-APM by the mineral acid during the reduction and requires the step of neutralizing the aqueous solution with a base subsequent to the reduction. It is also impossible to avoid mixing of salts, which have been formed from such mineral acid and base, in α-APM so isolated, resulting in a reduction in the quality of Aspartame.

Japanese Patent Publication No. 25538/1982 discloses a process for the preparation of α-APM, in which N-benzyloxycarbonylaspartic anhydride and L-phenylalanine methyl ester are reacted in an organic aliphatic solvent, the resultant Z-α-APM is, either after isolation or without isolation, subjected to catalytic hydrogenation in the presence of at least one catalyst selected from the group consisting of iron-group catalysts and platinum-group catalysts, resulting α-APM is dissolved in an aqueous solution of a mineral acid, and the solution is then neutralized. The Z-α-APM so obtained is, however, in a solid form unsuited for reduction, and it is difficult to grind the same. This process is accompanied by the additional drawbacks that, like the above-described process due to the use of the aqueous solution of the mineral acid, α-APM is hydrolyzed to byproduce α-AP having no sweetness and inorganic salts are undesirably mixed in the α-APM so purified.

In any of the conventional art described above, use of N-benzyloxycarbonyl-L-aspartic acid as a starting material makes it impossible to avoid byproduction of β-APM besides α-APM as the target product. This β-APM does not have sweetening effects but conversely gives bitterness so that its inclusion lowers the commercial value of α-APM.

As a process for isolating α-APM from such a mixture of α-APM and β-APM, Japanese Patent Publication No. 6305/1974 discloses a process in which α-APM and β-APM are brought into contact with β-resorcylic acid in an aqueous medium to convert α-APM into a sparinglysoluble addition product so that α-APM is separated from β-APM as an impurity. Although this process can separate α-APM from the impurity contained in a large amount, it requires cumbersome operation due to the use of β-resorcylic acid in the same amount as α-APM and β-APM and the recrystallization of the α-APM addition product from water subsequent to its isolation from a dilute aqueous solution thereof and, moreover, it is economically disadvantageous because the recovery rate of the expensive α-APM is low.

On the other hand, Japanese Patent Publication No. 41425/1974 discloses a process in which α-APM containing β-APM is brought into contact with a hydrohalogenic acid in an aqueous medium to form the sparingly-soluble hydrohalide of α-APM, thereby separating β-APM copresent as an impurity. This separation process which is conducted using an aqueous solution of the hydrohalogenic acid in an excess amount is good in separating β-APM from α-APM in which the β-APM is contained. It is, however, accompanied by such drawbacks that, because of the dissolution in the aqueous solution of the hydrohalogenic acid, hydrolysis of the methyl ester of α-APM tends to proceed, the recovery rate of the hydrohalide of α-APM is low and an expensive acid-resistant material must be used as a material for a reactor.

To obtain α-APM from a mineral acid salt of α-APM once isolated as an acid addition product as described above, a neutralization step is needed. This neutralization is generally conducted by dissolving the mineral acid salt of α-APM in water, adding a base to the solution to neutralize the same and then separating α-APM formed as crystals. Since α-APM is lost in a substantial amount in the aqueous solution, the yield becomes low. The filtrate contains a large amount of salts formed from the mineral acid and the base, so that it is difficult to use it again in the preceding step. As α-APM isolated in this manner contains salts in a large amount, operations such as recrystallization and desalting are needed to obtain the final product so that the yield is lowered further.

As has been described above, the previously-known preparation processes of α-APM are accompanied by one or more drawbacks and are not fully satisfactory as industrial preparation processes. To solve the problems in the conventional reducing steps of Z-α-APM, in particular, it is desired to conduct a reducing reaction in an aqueous medium. However, no process has heretofore been available to efficiently obtain an aqueous Z-α-APM suspension suited for reduction in such an aqueous solvent. Moreover, no process has been found for obtaining α-APM with high purity in high yield upon isolation of α-APM subsequent to catalytic reduction of Z-α-APM containing Z-β-APM.

SUMMARY OF THE INVENTION

An object of the present invention is to provide a process for the industrial and efficient preparation of α-APM having low impurity content in high yield.

The present inventors have proceeded with an extensive investigation in order to overcome the problems described above. As a result, it has been found that the use of an aqueous suspension of Z-α-APM in the form of fine particles upon preparation of α-APM by catalytic reduction of Z-α-APM in an aqueous solvent allows the reaction to proceed quick and moreover to reduce the formation of byproducts, especially L-aspartyl-L-aspartyl-L-phenylalanine methyl ester having 4 isomers because of combinations of α and β. It has also been found that, where Z-α-APM containing 30 wt. % or less of Z-β-APM is used as a raw material, the ratio of the α-isomer to the β-isomer (α/β ratio) after catalytic hydrogenation and the isolation yield α-APM can be both improved when an aqueous solution of Z-α-APM is reduced in the presence of a platinum-group catalyst, the catalyst is removed at a temperature at which α-APM so formed is completely dissolved, the filtrate is cooled to a temperature at which β-APM does not crystallize out, α-APM so crystallized is collected and then recrystallized from an aqueous solution, and the aqueous solution separated in the recrystallization step and containing α-APM is recycled for use in the aqueous suspension of Z-α-APM, leading to the completion of the present invention.

According to the process of this invention, an aqueous solution of α-APM can be obtained in a high yield and a short reaction time by the reducing reaction of Z-α-APM. Further, α-APM can be obtained by simply cooling the reaction mixture subsequent to elimination of the catalyst and, if necessary, toluene therefrom. Its recrystallization can provide α-APM with high purity. By reutilizing an aqueous solution, which is separated in the recrystallization step and contains α-APM, in the reducing step of Z-α-APM, the ratio of α-APM to β-APM after the reduction becomes greater than the α/β ratio of the starting Z-APM so that a high yield can be achieved upon crystallization and separation of α-APM under conditions not permitting crystallization of β-APM in the crystallizing step. In addition, the aqueous solution separated from the recrystallization step can be used again without the need for processing it through such steps as heating and concentration, so that impurities such as DKP and α-AP are not formed. Moreover, a-APM can be obtained from Z-APM without using any mineral acid. No neutralization step is therefore needed. α-APM so prepared, therefore, does not contain any salt which would otherwise be formed from the mineral acid and a base. As has been described above, the processes of the present invention can be employed industrially for the efficient preparation of high-purity α-APM substantially free of impurities.

DETAILED DESCRIPTION OF THE INVENTION

In a first aspect of this invention, there is thus provided a process for the preparation of α-L-aspartyl-L-phenylalanine methyl ester by catalytic hydrogenation of N-benzyloxycarbonyl-a-L-aspartyl-L-phenylalanine methyl ester, which comprises conducting said catalytic hydrogenation in an aqueous suspension containing the N-benzyloxycarbonyl-a-L-aspartyl-L-phenylalanine methyl ester in the form of particles whose average particle size is not greater than 800 μm.

In a second aspect of this invention, there is also provided a process for the preparation of α-L-aspartyl-L-phenylalanine methyl ester, which comprises reducing an aqueous suspension of N-benzyloxycarbonyl-a-L-aspartyl-L-phenylalanine methyl ester, said ester containing not more than 30 wt. % of N-benzyloxy-β-L-aspartyl-L-phenylalanine methyl ester, with hydrogen in the presence of a platinum-group catalyst, filtering off the catalyst, cooling the filtrate to a temperature at which β-L-aspartyl-L-phenylalanine methyl ester does not crystallize out, collecting α-L-aspartyl-L-phenylalanine methyl ester so collected, dissolving the thus-collected filtrate in an aqueous solvent at an elevated temperature, cooling the resulting solution, collecting crystallized α-L-aspartyl-L-phenylalanine methyl ester and washing the same to obtain purified α-L-aspartyl-L-phenylalanine methyl ester, and recycling the aqueous solution, which has been separated in the purification step and contains α-L-aspartyl-L-phenylalanine methyl ester, for use in the aqueous suspension of Z-α-APM.

A primary feature of the first aspect of this invention resides in the use of an aqueous suspension of Z-α-APM in the form of fine particles upon catalytic hydrogenation of Z-α-APM in an aqueous solvent. The raw material, Z-α-APM, is obtained usually by reacting N-benzyloxycarbonylaspartic anhydride (hereinafter abbreviated as "Z-Asp anhydride") with L-phenylalanine methyl ester (hereinafter abbreviated as "L-PM") in an organic solvent and contains a small amount of unreacted Z-Asp anhydride. When this Z-α-APM is subjected to catalytic hydrogenation in an organic solvent miscible with water, such as acetic acid, the resulting α-APM reacts with the Z-Asp anhydride, followed by catalytic hydrogenation so that two isomers, α-L-aspartyl-α-L-aspartyl-L-phenylalanine methyl ester and β-L-aspartyl-α-L-aspartyl-L-phenylalanine methyl ester, are formed. Where the raw material, Z-α-APM, contains Z-β-APM, four isomers (hereinafter collectively abbreviated as "A₂PM") are formed because of combinations of α and β. It has, however, been found that the production of A₂PM is reduced when this reducing reaction is conducted in an aqueous solvent. If an aqueous suspension of Z-α-APM having a rather large particle size is employed, its effects are small. The use of fine Z-α-APM can significantly lower the production of A₂PM.

Z-α-APM employed in the process according to the first aspect of the present invention may contain Z-β-APM as an impurity.

According to the second aspect of the present invention,
- (a) Z-α-APM containing not more than 30 wt. % of Z-β-APM is suspended in an aqueous solvent, followed by catalytic hydrogenation in the presence of a platinum-group catalyst,
- (b) the catalyst is removed from the reaction mixture, which has been obtained in step (a), at such a temperature that the resulting α-APM is dissolved in toto and, if necessary, byproduced toluene is removed by phase separation,
- (c) an aqueous solution obtained in step (b) is cooled to such a temperature that β-APM does not crystallize out, and crystallized α-APM is subjected to solid-liquid separation, thereby obtaining crude APM,
- (d) the crude APM obtained in step (c) is dissolved at an elevated temperature in an aqueous solvent and then cooled to crystallize α-APM, and the α-APM so crystallized is subjected to solid-liquid separation, followed by washing to obtain purified APM, and
- (e) the fraction of an aqueous solution obtained by the solid-liquid separation and washing in step (d) and containing α-APM is reutilized as the aqueous solvent in step (a).

A primary feature of the second aspect of the present invention resides in the reutilization of the fraction of the aqueous solution, which has been separated in step (d) and contains α-APM, as the aqueous solvent in the catalytic hydrogenation step (a).

In the fraction of the aqueous solution separated in the recrystallization step, α-APM is contained, for example, in an amount of about 0.6 g per 100 g of the filtrate or washing when recrystallized at 5° C. although the amount of α-APM varies depending on the temperature of recrystallization and the amount of a washing solvent. The aqueous solution fraction also contains β-APM or DKP which is not suitable as a sweetener. It is however not desirable to discard β-APM or DKP as it is, because its discard results in a reduction in yield. It is therefore necessary to recycle it to a preceding step.

It is technically possible to recirculate the fraction of the aqueous solution, which is separated in step (d), as it is within step (d). According to this method, however, β-AMP, DKP and the like accumulate in the recycled aqueous solution so that the final product is mixed with these impurities.

When the fraction of the aqueous solution containing α-APM, said fraction having been separated in step (d), is recycled to the reducing step of Z-APM in step (a) as in the present invention, byproducts such as β-APM and DKP are excluded in the solution separated upon isolation of the crude APM in step (c) and is separately hydrolyzed to collect L-phenylalanine and L-aspartic acid. These byproducts therefore do not give any substantial effects to the next step, i.e., step (d), whereby they do not accumulate in the solution recycled to and reused in step (a). Accordingly, the purified APM obtained from step (d) is isolated from a low-impurity crude concentrate under the same conditions every time so that the purified APM has stable high-purity quality. Since α-APM is contained in the solution recycled from step (d), the ratio of α-APM to β-APM in the solution after the reducing reaction in step (a) is greater than the ratio of Z-α-APM to Z-β-APM in the raw material so that the efficiency of separation between α-APM and β-APM in step (c) becomes high. The overall yield of α-APM based on Z-α-APM during steps (a) to (d) becomes higher.

Any Z-β-APM-containing Z-α-APM can be used in the second aspect of this invention irrespective of its synthesis process. Z-α-APM containing Z-β-APM in an amount not greater than 30 wt. % can however be employed effectively for the following reasons. Since α-APM and β-APM have substantially the same solubility in water, inclusion of Z-β-APM in an amount greater than 30 wt. % results in low yield of α-APM even when the filtrate is cooled, after removal of a reducing catalyst by filtration, to such a temperature that β-APM does not crystallize out and crystallized α-APM is isolated. A large amount of α-APM is therefore lost together with β-APM in the filtrate so that the efficiency is impaired.

In both the first and second aspects of the present invention, the starting material, i.e., Z-α-APM may contain an organic solvent in a small amount insofar as the organic solvent does not inhibit crystallization of α-APM in steps (c) and (d). Specific examples of the organic solvent include lower aliphatic alcohols such as methyl alcohol, ethyl alcohol, n-propyl alcohol and isopropyl alcohol; ethers such as tetrahydrofuran and dioxane; nitriles such as acetonitrile and propionitrile; organic carboxylic acids such as formic acid, acetic acid and propionic acid; aromatic hydrocarbons such as benzene, toluene and xylene; and chlorinated hydrocarbons such as dichloromethane and 1,2-dichloroethane.

The Z-α-APM suspension employed in the process of this invention can be prepared by mixing water with a solution of Z-α-APM in an organic solvent.

- (1) If an organic solvent is miscible with water, it is only necessary to separate crystallized Z-α-APM by filtration or the like and then to suspend it in water. Examples of such an organic solvent include organic carboxylic acids such as acetic acid and propionic acid; amides such as dimethylformamide, dimethylacetamide and N,N'-dimethylimidazolidinone; and ketones such as acetone, methyl ethyl ketone and methyl isopropyl ketone.

To obtain fine particulate Z-α-APM in the process described above, it is preferable to add water to an organic solvent containing Z-α-APM upon mixing water with the organic solvent containing Z-α-APM. Such mixing is performed generally in a crystallizer equipped with a stirrer. It is preferred to increasing the stirring velocity because the particle system of Z-α-APM becomes smaller as the stirring speed is fast during the mixing. The mixing is usually conducted at 0.1 m/sec or faster, preferably at 0.2 m/sec or higher in terms of the end linear speed of a stirring blade.

- (2) Even if an organic solvent is not miscible with water, it can still be used in the process of this invention provided that it forms an azeotrope with water or it has a boiling point lower than water. Namely, an aqueous suspension can be prepared by distilling off the organic solvent after mixing the organic solvent, in which Z-α-APM is contained, with water. Examples of such an organic solvent include hydrocarbons such as benzene, toluene and n-hexane; and esters such as ethyl acetate, butyl acetate, amyl acetate, methyl propionate and ethyl propionate.

Although no particular limitation is imposed on the concentration of Z-α-APM in an organic solvent in the process described above, the concentration may generally range from 5% to 30%. When the reaction between N-benzyloxycarbonyl-L-aspartic anhydride and L-phenylalanine methyl ester is conducted in the above-described organic solvent, the reaction mixture can be used as it is.

When an organic solvent immiscible with water is used, it is possible to prepare a solution of Z-α-APM in the organic solvent, to mix the solution at once with water and then to distill off the organic solvent. According to this method, precipitated Z-α-APM crystals tend to stick together so that the particle size tends to become greater. To obtain an aqueous suspension of fine particulate Z-α-APM, the organic solvent is distilled off while adding the organic solvent solution dropwise into water. This method makes it possible to obtain a suspension containing Z-α-APM having a small, uniform particle size, whereby the reaction velocity in the subsequent reducing step becomes higher and the formation of byproducts is substantially reduced.

Distillation of the organic solvent is conducted at 60° C. or lower. If the temperature is higher than 60° C., crystallized Z-α-APM stick together so that the particle size increases. As a result, the velocity of the subsequent reducing reaction is extremely retarded, resulting in the formation of byproducts. The particle size of Z-α-APM in an aqueous Z-α-APM suspension in the reducing reaction is usually 10–800 μm. The smaller the particle size, the faster the reducing reaction. The shorter the reaction time, the smaller the production of impurities such as α-AP and DKP and the higher the yield of α-APM. Preferably, a suspension of Z-α-APM in an average particle size not greater than 200 μm is used for reduction.

The aqueous solvent in which the catalytic hydrogenation is performed in accordance with this invention is either water or a mixture of water and a lower alcohol. Illustrative of the lower alcohol include methanol, ethanol and propanol, with methanol being particularly preferred. This aqueous solvent may contain one or more other organic solvent in a small amount.

Examples of catalysts usable in the reduction include platinum-group catalysts such as palladium, platinum, cobalt, nickel, ruthenium and rhodium. Of these, palladium is particularly suited. For example, palladium-carbon is preferred. Although no particular limitation is imposed on the amount of the catalyst, it is preferable to use the catalyst in an amount of 0.5–10 wt. % based on Z-APM.

The reduction can be carried out either under normal pressure or elevated pressure.

The reducing temperature in the present invention is 80° C. or lower, preferably 40°–60° C. As the reducing time, 2–10 hours are generally sufficient although it varies depending on the temperature.

Although no particular limitation is imposed on the concentration of Z-α-APM in the aqueous suspension in the process of this invention, it may generally range from about 3% to about 20%. If the concentration of a suspension so prepared exceeds 20%, such a high concentration is not preferred because stirring of the suspension becomes difficult and the particle size of Z-α-APM becomes greater. Concentrations lower than about 3% are, however, not economical because the volume efficiency is low. If the concentration is high, α-APM formed subsequent to reduction is not completely dissolved but takes the form of a slurry so that the catalyst cannot be filtered off as it is. The reducing reaction can however be brought to completion even in such a state. Even in such a case, the catalyst can still be filtered off by adding a solvent or raising the temperature of the reaction mixture and dissolving α-APM.

The temperature at which the catalyst is filtered off subsequent to the reduction is not lower than the temperature at which the resulting α-APM and the like are completely dissolved. At 80° C. or higher, α-L-aspartyl-L-phenylalanine and DKP are formed by the hydrolysis of α-APM and the like and intramolecular cyclization, respectively, whereby the isolation yield of α-APM is lowered. The catalyst is filtered off preferably at 40°–60° C. The concentration of α-APM upon filtering off the catalyst is preferably near that of the saturated solution of α-APM at the temperature. The concentration can be about 2–4 wt. % at the temperature of 40°–60° C. At concentrations significantly lower than the above concentration, less crystals can be crystallized out upon cooling so that the yield drops.

The toluene formed by the removal of the benzyloxycarbonyl group is usually removed by phase separation subsequent to removal of the catalyst, although the toluene can be eliminated by causing it to evaporate during or after the reducing reaction.

After the catalyst is filtered off and, if necessary, toluene is separated, the filtrate can be cooled to collect crystals of crude α-APM. No particular limitation is imposed on the cooling means. When indirect cooling is applied, the cooling can be effected either by forced-convection heat transfer including mechanical agitation or by conduction heat transfer. As a direct cooling method, the solvent can be caused to evaporate under reduced pressure conditions so that cooling can be effected relying upon its latent heat of evaporation.

Any crystallizing temperature can be employed as long as it is higher than a predetermined temperature at which β-APM becomes saturated. It is however desirable to conduct the crystallization at a temperature as low as possible so that the yield can be increased.

As a method for subjecting the precipitated crystals of crude α-APM to solid-liquid separation, a conventional method such as filtration or centrifugal separation can be used.

As a method for purifying the thus-obtained crude α-APM by recrystallizing it from an aqueous solvent, the crude α-APM is dissolved to a concentration of 2–4 wt. % at a temperature not higher than 80° C., preferably at 40°–60° C. The resultant solution is cooled to 5° C. or lower. Crystals of α-APM so precipitated are collected by filtration and then washed, whereby α-APM completely free of β-APM is isolated. An aqueous solution of α-APM separated here is recycled and reused in the reduction of Z-APM in step (a). The combined aqueous solution of the filtrate and the washing generally has the following composition: about 0.6 wt.% α-APM, about 0.065 wt. % β-APM, about 0.01 wt. % DKP, and about 0.01 wt. % α-AP. The reutilization of the aqueous solution in the reducing step of Z-APM as described above makes it possible to render the ratio of α-APM to β-APM in the reducing step higher than the α/β ratio of the starting Z-APM, so that the crystallization and separation of the α isomer can be facilitated.

The processes of the present invention will hereinafter be described in detail by the following examples.

REFERENTIAL EXAMPLE 1

A solution of L-phenylalanine methyl ester (358.4 g) in acetic acid (658.8 g) and a solution of N-benzyloxycarbonylaspartic anhydride (505.9 g) in acetic acid (4382 g) were reacted at 15°–20° C. for 3 hours, followed by the concentration of the resultant reaction mixture to 1813 g. The concentrate was added dropwise at 25° C. over 30 minutes into water (3530 g) under stirring at 300 rpm in a 10l reactor which was equipped with a stirring blade of 15 cm in span. A mixture of Z-α-APM and Z-β-APM so crystallized was collected by filtration and dried, whereby Z-APM crystals (856.9 g) were obtained. As a result of an analysis by high performance liquid chromatography (HLC), the crystals were found to contain Z-α-APM (658.1 g) and Z-β-APM (164.5 g).

EXAMPLE 1

A solution of Z-APM (100 g), which had been obtained in Referential Example 1 and contained Z-α-APM (76.8 g, 0.179 mol), in acetic acid (137.17 g) was poured into water (369.5 g) under stirring by a stirring blade having a 10 cm span and driven at 400 rpm. Crystallized Z-α-APM was collected by filtration. To the thus-obtained wet cake (201.0 g) which contained Z-α-APM (72.40 g) having an average particle size of 90 μm, water (1348.4 g) was added. 5% Palladium carbon . (50% wet, 2.93 g) was added, followed by catalytic hydrogenation at 60° C. The reaction was completed in 3 hours. The solution obtained subsequent to the removal of the catalyst by filtration was found to contain α-APM (48.74 g, 0.1656 mol), DKP (0.30 g), α-AP (0.21 g) and A$_2$PM (0.0146 g).

EXAMPLE 2

A solution of Z-APM (100 g), which had been obtained in Referential Example 1 and contained Z-α-APM (76.8 g, 0.179 mol), in acetic acid (137.17 g) was poured into water (369.53 g) under stirring by a stirring blade having a 10 cm span and driven at 200 rpm. Crystallized Z-α-APM was collected by filtration. To the thus-obtained wet cake (201.0 g) which contained Z-α-APM (72.4 g) having an average particle size of 600 μm, water (1348.4 g) was added. 5% Palladium carbon (50% wet, 2.93 g) was added, followed by catalytic hydrogenation at 60° C. The reaction was completed in 3 hours. The solution obtained subsequent to the removal of the catalyst by filtration was found to contain α-APM (48.74 g, 0.1656 mol), DKP (0.30 g), α-AP (0.21 g) and A$_2$PM (0.0054 g).

COMPARATIVE EXAMPLE 1

A solution of Z-APM (100 g), which had been obtained in Referential Example 1 and contained Z-α-APM, (76.8 g, 0.179 mol), in acetic acid (137.17 g) was poured into water (369.53 g) under stirring by a stirring blade having a 10 cm span and driven at 400 rpm. Crystallized Z-α-APM was collected by filtration. To the thus-obtained wet cake (200.97 g) which contained Z-α-APM (72.40 g) having an average particle size of 3000 μm, water (1348.4 g) was added. 5% Palladium carbon (50% wet, 2.93 g) was added, followed by catalytic hydrogenation at 60° C. for 5 hours. The reaction was, however, not brought to completion. The filtrate obtained subsequent to the removal of the catalyst by filtration was found to contain Z-α-APM (31.9 g, 0.07453 mol), α-APM (27.26 g, 0.09263 mol), DKP (0.98 g), α-AP (2.08 g) and A$_2$PM (0.0054 g).

EXAMPLE 3

A solution of L-phenylalanine methyl ester (17.83 g) in 1,2-dichloroethane (55.72 g, hereinafter abbreviated as "EDC") and a solution of N-benzyloxycarbonylaspartic anhydride (26.0 g) in EDC (370.5 g) were condensed at 15°–20° C. for 3 hours. A solution of the thus-obtained Z-α-APM (35.37 g) and Z-β-APM (7.25 g) in EDC (426.21 g) was added dropwise to water (749.37 g) at 40° C. under reduced pressure over 1 hour while the EDC was distilled off, so that a suspension (777.7 g) was obtained. Z-α-APM and Z-β-APM were both found to have an average particle size of 120 μm.

EXAMPLE 4

A solution of Z-α-APM (40.96 g), which had been obtained in Referential Example 1, in ethyl acetate (426.21 g) was added dropwise to water (749.37 g) at 60° C. under reduced pressure over 1 hour while the ethyl acetate was distilled off, so that a suspension (725.2 g) was obtained. The average particle size of Z-α-APM was found to be 170 μm.

EXAMPLE 5

A solution of Z-α-APM (40.96 g), which had been obtained in Referential Example 1, in chloroform (426.21 g) was maintained at 40° C. under reduced pressure, to which water (749.47 g) was added dropwise over 1 hour while the chloroform was distilled off at 60° C. A suspension (750 g) was obtained. The average particle size of Z-α-APM was found to be 650 μm.

EXAMPLE 6

A solution of Z-α-APM (48.33 g, 0.1128 mol), which had been obtained in Referential Example 1, in butyl acetate (576.0 g) was added to water (780 g). The butyl acetate was then distilled off under reduced pressure at 45° C. for 1 hour, whereby a suspension (796 g) was obtained. The average particle size of Z-α-APM was found to be 220 μm. 5% Palladium carbon (50% wet, 2.87 g) was thereafter added, followed by catalytic hydrogenation at 60° C. The reaction was completed in 3 hours. The solution obtained subsequent to the removal of the catalyst by filtration was found to contain α-APM (31.56 g), DKP (0.51 g), α-AP (0.63 g) and A$_2$PM (0.025 g).

EXAMPLE 7

A solution of Z-α-APM (23.33 g, 0.05446 mol), which had been obtained in Referential Example 1, in EDC (221.74 g) was added dropwise to water (377.8 g) at 40° C. under reduced pressure over 1 hour while the EDC was distilled off, so that a suspension (403.5 g) was obtained. The average particle size of Z-α-APM was found to be 110 μm. Water (131.8 g) was then added and 5% palladium carbon (50% wet, 1.08 g) was also added, followed by catalytic hydrogenation at 60° C. The reaction was completed in 3 hours. A solution obtained subsequent to the removal of the catalyst by filtration was found to contain α-APM (15.50 g, 0.05267 mol), DKP (0.17 g), α-AP (0.32 g) and A$_2$PM (0.005 g).

COMPARATIVE EXAMPLE 2

A solution of Z-α-APM (40.96 g, 0.09561 mol) in EDC (426.21 g) was added dropwise to water (749.37 g) at 80° C. under reduced pressure over 1 hour while the EDC was distilled off, so that a suspension (649.7 g) was obtained. The average particle size of Z-α-APM was found to be 1200 μm. Water (402.3 g) was then added and 5% palladium carbon (50% wet, 2.15 g) was added further, followed by catalytic reduction at 80° C. for 6 hours. The reaction was, however, not brought to completion. The solution obtained subsequent to the removal of the catalyst by filtration was found to contain Z-α-APM (7.84 g, 0.01830 mol), α-APM (16.47 g, 0.05596 mol), DKP (3.97 g), α-AP (0.53 g) and A₂PM (0.09 g).

EXAMPLE 8

A mixture of Z-β-APM (8.6 g) and Z-α-APM (34.2 g) was suspended in water (610 g), to which 5% palladium-carbon (0.9 g) was added. After the resultant mixture was subjected to catalytic reduction under normal pressure at 60° C. for 2 hours, the catalyst was filtered off at the same temperature. After the toluene layer was separated, the water layer was gradually cooled and then stirred at 5° C. for 1 hour. At the same temperature, precipitated crystals were collected by filtration and then washed so that a wet α-APM cake (64.0 g) was isolated.

The thus-isolated wet α-APM cake was added with water (472.7 g) and dissolved in the latter at 60° C. The solution so obtained was gradually cooled and then stirred at 5° C. for 1 hour. At the same temperature, precipitated crystals were collected by filtration, washed with water and then dried, whereby α-APM (15.6 g) was isolated. At the same time, a filtrate-washing mixture (537.5 g) containing α-APM (3.7 g) and β-APM (0.4 g) was also obtained.

The crystals so obtained was analyzed by high performance liquid chromatography. As a result, it were found that the content of α-APM was 15.1 g (64.0% based on Z-α-APM) and β-APM was not contained at all.

A mixture of Z-β-APM (8.6 g) and Z-α-APM (34.2 g) was suspended in a mixture of the recrystallization filtrate-washing mixture (528 g) and water (227 g), to which 5% palladium-carbon (0.9 g) was added. After the resultant mixture was subjected to catalytic reduction under normal pressure at 60° C. for 2 hours, the catalyst was filtered off at the same temperature and the toluene layer was then separated. The water layer was gradually cooled to 5° C. and, at the same temperature, precipitated crystals were collected by filtration and then washed, whereby a wet α-APM cake (75.1 g) was isolated.

The thus-isolated wet α-APM cake was added with water (529.4 g) and dissolved in the latter at 60° C. The solution so obtained was gradually cooled and then stirred at 5° C. for 1 hour. At the same temperature, precipitated crystals were collected by filtration, washed with water and then dried, whereby α-APM (18.4 g) was isolated. At the same time, a filtrate-washing mixture (623.2 g) containing α-APM (4.1 g) and β-APM (0.4 g) was also obtained.

The crystals so obtained were analyzed by high performance liquid chromatography. As a result, it was found that the content of α-APM was 17.9 g (76.2% based on Z-α-APM) and β-APM was not contained at all. In addition, the contents of Cl, SO₄ and Na ions were all found to be 10 ppm or less.

EXAMPLE 9

A mixture of Z-β-APM (8.6 g) and Z-α-APM (34.2 g) was suspended in a mixture of the recrystallization filtrate-washing mixture (610.7 g), which had been obtained in Example 8, and water (117.1 g), to which 5% palladium-carbon (0.9 g) was added. After the resultant mixture was subjected to catalytic reduction under normal pressure at 40° C. for 3 hours, precipitated crystals were dissolved at 60° C., the catalyst was filtered off at the same temperature and the toluene layer was then separated. The water layer was gradually cooled to 5° C. and stirred for 1 hour and, at the same temperature, precipitated crystals were collected by filtration and then washed, whereby a wet α-APM cake (77.1 g) was isolated.

The thus-isolated wet α-APM cake was added with water (539.5 g) and dissolved in the latter at 60° C. The solution so obtained was gradually cooled and then stirred at 5° C. for 1 hour. At the same temperature, precipitated crystals were collected by filtration, washed with water and then dried, whereby α-APM (18.5 g) was isolated. At the same time, a filtrate-washing mixture (635.8 g) containing α-APM (4.2 g) and β-APM (0.4 g) were also obtained.

The crystals so obtained was analyzed by high performance liquid chromatography. As a result, it was found that the content of α-APM was 17.9 g (76.2% based on Z-α-APM) and β-APM was not contained at all.

EXAMPLES 10–17

Reutilizing the recrystallization filtration of Example 9, an operation was conducted in a similar manner to Example 9.

The above operation was repeated 8 times. The isolation yields of α-APM in Examples 8–17 are shown in Table 1.

TABLE 1

| Example | Isolation yield (based on Z-α-APM) |
|---|---|
| 8 | 76.2% |
| 9 | 76.2% |
| 10 | 76.2% |
| 11 | 76.2% |
| 12 | 76.1% |
| 13 | 76.2% |
| 14 | 76.2% |
| 15 | 76.0% |
| 16 | 76.2% |
| 17 | 76.1% |

β-APM was not contained at all in any samples obtained in the examples up to Example 17.

EXAMPLE 18

A mixture of Z-β-APM (12.8 g) and Z-α-APM (30 g) was suspended in water (529.5 g), to which 5% palladium-carbon (0.9 g) was added. After the resultant mixture was subjected to catalytic reduction under normal pressure at 60° C. for 2 hours, the catalyst was filtered off at the same temperature. After the toluene layer was separated, the water layer was gradually cooled and then stirred at 5° C. for 1 hour. At the same temperature, precipitated crystals were collected by filtration and then washed so that a wet α-APM cake (50.0 g) was isolated.

The thus-isolated wet α-APM cake was added with water (350.0 g) and dissolved in the latter at 60° C. The solution so obtained was gradually cooled and then stirred at 5° C. for 1 hour. At the same temperature, precipitated crystals were collected by filtration, washed with water and then dried, whereby α-APM (11.9 g) was isolated. At the same time, a filtrate-washing mixture (420.3 g) containing α-APM (2.9 g) and β-APM (11.9 g) was also obtained.

The crystals so obtained were analyzed by high performance liquid chromatography. As a result, it was found that the content of α-APM was 11.5 g (55.8% based on Z-α-APM) and β-APM was not contained at all.

EXAMPLE 19

A mixture of Z-β-APM (12.8 g) and Z-α-APM (34.2 g) was suspended in a mixture of the recrystallization filtrate-washing mixture (411.9 g), which had been obtained in Example 18, and water (196.4 g), to which 5% palladium-carbon (0.9 g) was added. After the resultant mixture was subjected to catalytic reduction under normal pressure at 60° C. for 2 hours, the catalyst was filtered off at the same temperature and the toluene layer was then separated. The water layer was gradually cooled to 5° C. and stirred for 1 hour and, at the same temperature, precipitated crystals were collected by filtration and then washed, whereby a wet α-APM cake (58.7 g) was isolated.

The thus-isolated wet α-APM cake was added with water (396.9 g) and dissolved in the latter at 69° C. The solution so obtained was gradually cooled and then stirred at 50° C. for 1 hour. At the same temperature, precipitated crystals were collected by filtration, washed with water and then dried, whereby α-APM (13.5 g) was isolated.

The crystals so obtained were analyzed by high performance liquid chromatography. As a result, it was found that the content of α-APM was 13.1 g (63.6% based on Z-α-APM) and β-APM was not contained at all.

COMPARATIVE EXAMPLE 3

A mixture of Z-β-APM (10.7 g) and Z-α-APM (42.8 g) was suspended in methanol (235 ml), to which 1N-hydrochloric acid (210 ml) and 5% palladium-carbon (4.7 g) were added. After the resultant mixture was subjected to catalytic reduction under normal pressure at room temperature for 3 hours, the catalyst was filtered off and the methanol in the filtrate was distilled off under reduced pressure. Crystals so precipitated were collected by filtration at room temperature and then washed, whereby a wet cake (36.9 g) of α-APM hydrochloride was isolated.

The thus-isolated wet cake of α-APM hydrochloride was added with water (265 ml), followed by neutralization with 10% aqueous ammonia at room temperature. The resulting solution was cooled to 5° C., at which the solution was stirred for 1 hour. Crystals so precipitated were collected by filtration at the same temperature, washed with water and then dried, whereby α-APM (14.9 g) was isolated.

The crystals so obtained was analyzed by high performance liquid chromatography. As a result, it was found that the content of α-APM were 14.4 g (61.2% based on Z-α-APM) and β-APM was not contained at all. However, the content of Cl ions was found to be 300 ppm. Comparative Example 4 (Reutilization of filtrate and washing in recrystallization step).

A mixture of Z-β-APM (160.5 g) and Z-α-APM (642 g) was suspended in water (9150 g), to which 5% palladium-carbon (13.5 g) was added. After the resulting mixture was subjected to catalytic reduction under normal pressure at 60° C. for 3 hours, the catalyst was filtered off at the same temperature and the toluene layer was separated. The water layer was gradually cooled to 5° C. and stirred for 1 hour and, at the same temperature, precipitated crystals were collected by filtration and then washed, whereby a wet α-APM cake (960.7 g) was isolated.

A portion (64.0 g) of the thus-isolated wet α-APM cake was added with water (472.7 g) and dissolved in the latter at 60° C. The solution so obtained was gradually cooled and then stirred at 5° C. for 1 hour. At the same temperature, precipitated crystals were collected by filtration, washed with water and then dried, whereby α-APM (15.6 g) was isolated. At the same time, a filtrate-washing mixture (537.5 g) containing α-APM (3.7 g) and α-APM (0.4 g) was also obtained.

The crystals so obtained were analyzed by high performance liquid chromatography. As a result, it was found that the content of α-APM was 15.1 g (64.9% based on Z-α-APM) and β-APM was not contained at all.

A portion (64.0 g) of the wet α-APM cake was next taken, to which the recrystallization filtrate-washing mixture (528 g) was added to dissolve the former in the latter at 60° C. The resulting solution was gradually cooled and then stirred at 5° C. for 1 hour. At the same temperature, precipitated crystals were collected by filtration, washed with water and then dried, whereby α-APM (17.9 g) was isolated. The crystals so obtained were analyzed by high performance liquid chromatography. As a result, it was found that the content of α-APM was 17.4 g (76.2% based on Z-α-APM) and β-APM was not contained at all.

The above operation (reutilization of filtrate-washing mixture) was repeated 4 times. The isolation yields of α-APM are shown in Table 2.

TABLE 2

| Operation | Isolation yield (based on Z-α-APM) |
|---|---|
| 0th | 64.0% |
| 1st | 76.2% |
| 2nd | 76.0% |
| 3rd | 76.1% |
| 4th | 76.2% |
| 5th | 76.1% |

From the third reutilization, β-APM was contained at a concentration of 0.1–0.3% in the α-APM so isolated. It was therefore necessary to conduct recrystallization again.

EXAMPLE 20

A solution of L-phenylalanine methyl ester (60.6 g) in acetic acid (111.4 g) and a solution of N-benzyloxycarbonylaspartic anhydride (52.0 g) in acetic acid (741.0 g) were reacted at 15°–20° C. for 3 hours, followed by the concentration of the resultant reaction mixture to 306.6 g. The concentrate was added dropwise at 25° C. over 30 minutes into water (597.0 g) under stirring in a 1-l reactor which was equipped with a stirring blade having a 10 cm span and driven at 400 rpm. A mixture of Z-α-APM and Z-β-APM so crystallized was collected by filtration, whereby a wet cake having an average particle size of 90 μm was obtained. As a result of an HLC analysis, the crystals were found to contain Z-α-APM (113.8 g) and Z-β-APM (26.7 g).

A portion (146.8 g) of the wet cake was dissolved in a mixture of the recrystallization filtrate-washing mixture (610.7 g), which had been obtained in Example 13, and water (117.1 g), followed by the addition of 5%-palladium-carbon (0.9 g). After the resulting mixture was subjected to catalytic reduction under normal pressure at 60° C. for 2 hours, the catalyst was filtered off at the same temperature and the toluene layer was separated. The water layer was gradually cooled to 5° C. and stirred for 1 hour at the same temperature. Precipitated crystals were collected by filtration and then washed, whereby a wet cake (87.3 g) containing α-APM (26.2 g) was isolated. As a result of an HLC analysis, the content of impurities were found as follows, all based on α-APM: 0.6% DKP, 0.4% α-AP, and 0.03% A₂PM. The wet α-APM cake was added with water (522.0 g) and dissolved in the latter at 60° C. The solution so obtained was gradually cooled to 5° C. and, at the same temperature, was stirred for 1 hour. Crystals so precipitated were collected by filtration, washed with water and then dried, whereby α-APM (21.6 g) was obtained. As a result of an HLC analysis, it was found that the content of α-APM was 21.0 g (71.4% based on Z-α-APM) while the contents of impurities were 0.2% DIP, 0.1% α-AP and 0.03% A₂PM, and β-APM was not detected.

We claim:

1. A process for the preparation of α-L-aspartyl-L-phenylalanine methyl ester, which comprises (1) reducing an aqueous suspension of N-benzyloxycarbonyl-α-L-phenylalanine methyl ester, said ester containing not more than 30 wt. % of N-benzyloxy-β-L-aspartyl-L-phenylalanine methyl ester, with hydrogen in the presence of a platinum-group catalyst, (2) filtering off the catalyst, (3) cooling the filtrate to a temperature at which the α-L-aspartyl-L-phenylalanine methyl ester crystallizes out, but at which the β-L-aspartyl-L-phenylalanine methyl ester does not crystallize out, (4) collecting the α-L-aspartyl-L-phenylalanine methyl ester so crystallized, (5) dissolving the thus-collected crystals in an aqueous solvent at an elevated temperature, (6) cooling the resulting solution to a temperature at which α-L-aspartyl-L-phenylalanine methyl ester crystallizes out, (7) separating the crystallized α-L-asparty-L-phenylalanine methyl ester and the aqueous solution, (8) collecting the crystallized α-L-aspartyl-L-phenylalanine methyl ester and (9) washing the same to obtain purified α-L-aspartyl-L-phenylalanine methyl ester, and (10) recycling the aqueous solution and the washing, which have been separated and which contains the α-L-aspartyl-L-phenylalanine methyl ester, for use in the aqueous suspension.

2. The process of claim 1, wherein the N-benzyloxycarbonyl-α-L-aspartyl-L-phenylalanine methyl ester has been obtained by reacting N-benzyloxycarbonylaspartic anhydride and L-phenylalanine methyl ester in an organic solvent.

3. The process of claim 1, wherein the aqueous suspension contains particles whose average particle size is not greater than 800 μm.

4. The process of claim 3, wherein the aqueous suspension containing the particles whose average particle size is not greater than 800 μm has been obtained by mixing a solution of N-benzyloxycarbonyl-α-L-aspartyl-L-phenylalanine methyl ester in an organic solvent with water, separating precipitated crystals and suspending the crystals in an aqueous solution.

5. The process of claim 1, wherein the aqueous suspension has been obtained by mixing a solution of a mixture of N-benzyloxycarbonyl-α-L-aspartyl-L-phenylalanine methyl ester and N-benzyloxycarbonyl-β-L-aspartyl-L-phenylalanine methyl ester in an organic solvent with water and distilling off the organic solvent at a temperature not higher than 60° C.

6. The process of claim 5, wherein the aqueous suspension has been obtained by distilling off an organic solvent at a temperature not higher than 60° C. while adding dropwise into water a solution of a mixture of N-benzyloxycarbonyl-α-L-aspartyl-L-phenylalanine methyl ester and N-benzyloxycarbonyl-β-L-aspartyl-L-phenylalanine methyl ester in the organic solvent.

* * * * *

UNITED STATES PATENT AND TRADEMARK OFFICE
CERTIFICATE OF CORRECTION

PATENT NO. : 5,424,477

DATED : June 13, 1995

INVENTOR(S) : Chojiro HIGUCHI et al

It is certified that error appears in the above-indentified patent and that said Letters Patent is hereby corrected as shown below:

In claim 1, line 24, delete "L-phenylalanine methyl ester" and insert --L-aspartyl-L-phenylalanine methyl ester--; and line 38, delete "asparty" and insert --aspartyl--.

Signed and Sealed this

Twenty-seventh Day of May, 1997

Attest:

BRUCE LEHMAN

*Attesting Officer*     *Commissioner of Patents and Trademarks*